(12) United States Patent
Parasassi et al.

(10) Patent No.: US 8,637,573 B2
(45) Date of Patent: Jan. 28, 2014

(54) N-ACETYL-L-CYSTEINE FOR THE TREATMENT OF ENDOMETRIOSIS

(75) Inventors: Tiziana Parasassi, Rome (IT); Maria Grazia Porpora, Rome (IT)

(73) Assignee: Iasomai AB, Lidingö (SE)

( * ) Notice: Subject to any disclaimer, the term of this patent is extended or adjusted under 35 U.S.C. 154(b) by 0 days.

(21) Appl. No.: 13/428,984

(22) Filed: Mar. 23, 2012

(65) Prior Publication Data

US 2012/0238627 A1    Sep. 20, 2012

Related U.S. Application Data

(63) Continuation of application No. PCT/EP2010/064175, filed on Sep. 24, 2010.

(30) Foreign Application Priority Data

Sep. 25, 2009 (EP) .................................... 09171394

(51) Int. Cl.
*A61K 31/195* (2006.01)
*C07C 321/00* (2006.01)

(52) U.S. Cl.
USPC .......................................... 514/562; 562/557

(58) Field of Classification Search
USPC .......................................... 514/562; 562/557
See application file for complete search history.

(56) References Cited

FOREIGN PATENT DOCUMENTS

EP     2 305 238 B1    12/2011

OTHER PUBLICATIONS

Pittaluga et al., "More than antioxidant: N-acetyl-L-cysteine in a murine model of endometriosis," Fertility and Sterility, vol. 94, No. 7, Dec. 2010 (online publication date—Jul. 23, 2010), pp. 2905-2908.*

Parassai, T., et al., "Differentiation of normal and cancer cell induced by sulfhydryl reduction: biochemical and molecular mechanisms", Cell Death and Differentiation, 2005, pp. 1285-1296, vol. 12.
Gustafsson, Anna C., et al., "Global gene expression analysis in time series following N-acetyl L-cysteine induced epithelial differentiation of human normal and cancer cells in vitro", BMC Cancer, Jul. 7, 2005, pp. 1-19.
Ngo, et al., "Reactive Oxygen Species Controls Endometriosis Progression", The American Journal of Pathology, Jul. 2009, pp. 225-234, vol. 175, No. 1, American Society for Investigative Pathology, Paris, France.
Wu, et al., "Histone Deacetylase Inhibitors Trichostatin A and Valproic Acid Induce Cell Cycle Arrest and P21 Expression in Immortalized Human Endometrial Stromal Cells", Science Direct, European Journal of Obstetrics & Gynecology and Reproductive Biology, Feb. 18, 2007, pp. 198-203, vol. 137, Wisconsin, Milwaukee.
Foyouzi et al., "Effects of oxidants and antioxidants on proliferation of endometrial stromal cells", Fertility and Sterility, Oct. 2004, pp. 1019-1022, vol. 82, Suppl. 3, American Society for Reproductive Medicine, Elsevier Inc., U.S.A.
Murakami Takashi, Feature Article: Examination of Endometriosis, "Recurrence of Endometriosis and What to do," Obstetric and Gynecologic Treatment, Mar. 2008, vol. 96, No. 3, p. 307-311.
Obata et al., Feature Article: Examination of Endometriosis, "Symptoms and Diagnosis of Endometriosis," Obstetric and Gynecologic Treatment, Mar. 2008, vol. 96, No. 3, p. 255-260.

* cited by examiner

*Primary Examiner* — Shengjun Wang
*Assistant Examiner* — Jody Karol
(74) *Attorney, Agent, or Firm* — Haynes and Boone, LLP (57) ABSTRACT

The invention relates to a new prescription of NAC in the treatment of endometriosis and of indications associated with endometriosis, in a human or mammalian animal patient. In addition an effective dose regimen of NAC in the treatment of endometriosis is proposed. In one embodiment of the present invention the prescribed treatment regimen may be used e.g. in order to control the frequency and the intensity of pain symptoms (dysmenorrhea, dyspareunia and acyclic chronic pelvic pain), to reduce the size of endometriotic lesions eventually up to their disappearance, to reduce recurrences after surgery and/or to improve fertility. Side effects of this treatment are virtually absent and, in particular, this treatment does not hinder pregnancy.

9 Claims, 7 Drawing Sheets

Fig. 6 (Prior Art - metabolic effects on cancer treated with NAC)

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide 18S RNA Forward Primer

<400> SEQUENCE: 1
cgcggttcta ttttgttggt                                               20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide 18S RNA Reverse Primer

<400> SEQUENCE: 2
agtcggcatc gtttatggtc                                               20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide COX-2 Forward Primer

<400> SEQUENCE: 3
cccccacagt caaagacact                                               20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide COX-2 Reverse Primer

<400> SEQUENCE: 4
agttgctcat caccccactc                                               20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide MMP-9 Forward Primer

<400> SEQUENCE: 5
tgaatcagct ggcttttgtg                                               20

<210> SEQ ID NO 6
<211> LENGTH: 20
```

```
<212> TYPE: DNA
<213> ORGANISM: Artificial Sequence
<220> FEATURE:
<223> OTHER INFORMATION: Oligonucleotide MMP-9 Reverse Primer

<400> SEQUENCE: 6
gtggatagct cggtggtgtt                                                20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide P21 Forward Primer

<400> SEQUENCE: 7
tccacagcga tatccagaca                                                20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide P21 Reverse Primer

<400> SEQUENCE: 8
acgaagtcaa agttccaccg                                                20
```

N-ACETYL-L-CYSTEINE FOR THE TREATMENT OF ENDOMETRIOSIS

CROSS-REFERENCE TO RELATED APPLICATIONS

This application is a continuation of. PCT/EP2010/064175, filed Sep. 24, 2010, which in turn and claims priority to EP Patent Application No. 09171394.1, filed Sep. 25, 2009, the contents of both of which are incorporated herein by reference in their entirety.

FIELD OF THE INVENTION

The present invention relates to a pharmaceutical composition comprising N-acetyl-L-cysteine useful for the treatment of endometriosis and indications associated with endometriosis.

BACKGROUND

Endometriosis is the third leading cause of gynecologic hospitalization in the United States, and affecting an estimated 14 million women in Europe. Widely used numbers for the incidence of endometriosis include 5-10% of all reproductive age women and 30-40% of all women with an infertility problem. It is a disease characterized by the presence outside the uterine cavity of tissue which is histologically identical to endometrium, i.e. the membrane lining the inside of the mammalian uterus. This misplaced tissue develops into growths or lesions (also called implants or nodules) which respond to the menstrual cycle in the same way that the endometrial tissue of the uterus does: each month the tissue builds up, breaks down, and sheds. While menstrual blood flows out from the uterus, instead the blood and tissue shed from endometrial growths has no way of flowing out. This results in internal bleeding, breakdown of blood vessels and tissue from the lesions, and a consequent chronic inflammation.

The two most common symptoms of endometriosis are pain and infertility. Symptoms can include: dysmenorrhea, i.e. pain before or after menstrual periods, as well as pain during or after sex; pelvic chronic pain or lower back, intestinal, pain; heavy menstrual periods, or spotting and bleeding between periods; painful bowel movements or painful urination during menstrual periods; infertility.

The cause of endometriosis is presently not known and several theories have been proposed to give a reason to the ectopic migration and implant of endometrial cells. Recent evidences relate the occurrence of endometriosis to an altered condition of the tissue of origin itself: the eutopic endometrium. There is an increasing agreement within the art that uncontrolled migration, implant and growth of endometriomas originate from disorders in the eutopic endometrial cells. There is currently no cure for endometriosis. A variety of treatment options exist, and there are ways to minimize the symptoms caused by the condition. Besides the use of analgesics for treating pain, treatment of endometriosis is mainly related to the suppression of ovary function in estrogens secretion, therefore hormone treatments of various entities, up to the induction of menopause in the most severe cases. Surgery is used to remove endometriomas, adhesions, peritoneal implants and deep lesions located in the recto-vaginal septum or in other sites (i.e., bladder, bowel), and to relieve pain. However, recurrences occur after both medical and surgical treatments. Young women with endometriosis are often faced with difficult decisions regarding their future reproduction. Hormone treatment, being intended for the suppression of ovary function, is not compatible with pregnancy.

N-acetyl-L-cysteine (hereinafter referred to as NAC) is a well-known drug, which has been used mainly as a mucolytic agent and in the treatment of paracetamol poisoning. In recent years it has also been acknowledged as having other beneficial properties, such as being antiinflammatory and anti-proliferative, and has been suggested for the treatment of a variety of different disorders and symptoms such as schizophrenia, diabetes and cancer. In previous studies investigating the molecular mechanisms underlying and relating to endometriosis it has been proposed that the increased cell proliferation rates in endometriosis may be induced by oxidative stress in the endometriotic tissue, caused by free radicals or ROSs. It has thus been proposed that new therapeutic strategies for endometriosis may be based on antioxidants and ROS scavengers such as NAC.

PRIOR ART

Charlotte Ngo et. al. proposed (The American Journal of Pathology (2009), Vol. 175, No. 1, pages 225-234) that oxidative stress might induce or enhance the proliferation of the endometriotic cells in endometriosis. Antioxidants such as NAC were therefore suggested for the treatment of endometriosis. Studies on primary cell lines from patients with endometriosis as well as in a mouse model implanted with endometriotic tissue of human origin showed that NAC abrogated signs of oxidative stress as well as increased proliferation in the respective models. It was thus suggested that antioxidants such as NAC could be used as a safe and efficient treatment of endometriosis.

Nastaran Foyouzi et. al. also proposed (Fertility and Sterility (2004), Vol. 82, Suppl. 3, pages 1019-1022) that antioxidants such as NAC could be used for the treatment of endometriosis. The article discloses an in vitro study where cells isolated from healthy subjects as well as patients with endometriosis were treated with different antioxidant, e.g. NAC. All antioxidants inhibited proliferation of endometrial stromal cells.

In studies by Yan Wo and Sun-Wei Guo (Gynecologic and Obstetric Investigation (2006), Vol. 62, No. 4, pages 193-205; European Journal of Obstetrics & Gynecology and Reproductive Biology, (2008), Vol. 137, pages 198-203); patent document US 2007/0287676 A1) the effect of NAC on proliferation and cell cycle arrest in immortalized human endometrial stromal cells was investigated and compared to other agents proposed for the treatment of endometriosis. NAC was shown to have an effect on both proliferation and cell cycle arrest, although not as pronounced as compared with histone deacetylase inhibitors.

In a study by S. Estany et. al. (Journal of reproductive Immunology (2007), Vol. 75, pages 1-10) it was shown that the antioxidant activity of NAC and other antioxidative agents on endometrial cells in culture improved the viability of oxidized cells, by preventing H2O2 induced cell cytotoxicity.

Other related art include US2003/0190381 A1, WO2004/096206 A2, US6239137 B1, US2003/0119875 A1, US2004/0014672 A1 and WO2005/048822 A2.

Other background art, describing the molecular effect of NAC in the treatment of cancer, include T. Parasassi, et. al. (Cell Death and Differentiation (2005), Vol. 12, No. 10, pages 1285-1296); E. K. Krasnowska et. al. (Free Radicals Biology and Medicine 2008, 45(11): 1566-72) and A. C. Gustafsson et. al. (BMC Cancer (2005), 5:75).

OBJECTS OF THE INVENTION

The clinical outcome of NAC treatment in endometriosis has, to the knowledge of the inventors, not been determined in the prior art, nor has an efficient dosage regimen for the treatment of endometriosis or the use of NAC for the treatment of indications associated with endometriosis been proposed.

It is therefore a general object of the present invention to provide a solution to the problem of providing a pharmaceutical composition comprising N-acetyl-L-cysteine (NAC) for the treatment of endometriosis and indications associated with endometriosis in humans and mammals. An aspect of the object is to provide a pharmaceutical composition comprising N-acetyl-L-cysteine (NAC) for use with an effective dosage regimen for the treatment of endometriosis and of symptoms related to endometriosis in mammals, including humans.

SUMMARY OF THE INVENTION

It has previously been proposed that NAC could be used in new therapeutic strategies for endometriosis, based on its use as an antioxidant and a ROS scavenger. The inventors of the present disclosure show that NAC induces molecular and cellular changes that not only inhibit proliferation but also induce differentiation of the diseased tissue towards normal tissue.

These findings have led the inventors of the present invention to propose a new prescription of NAC in the treatment of endometriosis and of indications associated with endometriosis, in a human or mammalian animal patient. In addition an effective dose range of NAC in the treatment of endometriosis is proposed. In one embodiment of the present invention the prescribed treatment regimen may be used e.g in order to control the frequency and the intensity of pain symptoms (dysmenorrhea, dyspareunia and acyckic chronic pelvic pain), to reduce the size of endometriotic lesions eventually up to their disappearance, to reduce recurrences after surgery and/or to improve fertility. Side effects of this treatment are virtually absent and, in particular, this treatment does not hinder pregnancy.

The present invention provides a pharmaceutical composition comprising N-acetyl-L-cysteine for use in the treatment of a mammal, including a human, having endometriosis, where the composition is for pulsed or intermittent, oral administration, for a time period of two months or more, at a dose of N-acetyl-L-cysteine that is between 20 and 90 mg/kg/day on days when administered.

In one embodiment the invention provides a pharmaceutical composition comprising N-acetyl-L-cysteine for the above mentioned use where the composition is for administration for 3-5 consecutive days followed by 2-4 days of interruption. In another embodiment the pharmaceutical composition comprising N-acetyl-L-cysteine is for administration for 1-3 consecutive days, followed by 1-2 days of interruption.

In one embodiment the invention provides a pharmaceutical composition comprising N-acetyl-L-cysteine for the above mentioned use, where the composition is for administration at a dose of N-acetyl-L-cysteine that is between 30 and 60 mg/kg/day on days when administered. In another embodiment the pharmaceutical composition is for administration at a dose of N-acetyl-L-cysteine that is between 30 and 45 mg/kg/day on days when administered.

In one embodiment the invention provides a pharmaceutical composition comprising N-acetyl-L-cysteine for the use described above where the pharmaceutical composition is protected from light. In another embodiment the pharmaceutical composition is a water soluble tablet. In still another embodiment the pharmaceutical composition contains sodium hydrogen carbonate. In one embodiment the pharmaceutical composition is a slow-release formulation and/or a formulation for gastric protection.

In one embodiment the invention provides a pharmaceutical composition comprising N-acetyl-L-cysteine for use in treating pain caused by endometriosis. In another embodiment the pharmaceutical composition is for use in treating infertility caused by endometriosis. In still another embodiment the pharmaceutical composition is for use in pre-treating mammals having endometriosis before laparoscopy or surgery. In one embodiment the pharmaceutical composition is for use in treating mammals having endometriosis after laparoscopy or surgery, to prevent recurrences.

In one aspect the invention provides a method for the treatment of a mammal having endometriosis, comprising orally administering a pharmaceutical composition comprising N-acetyl-L-cysteine to said mammal in a pulsed or intermittent dosage regimen, for a time period of two months or more, at a dose of N-acetyl-L-cysteine that is between 20 and 90 mg/kg/day on days when administered. In one embodiment of the method the pharmaceutical composition is administered for 3-5 consecutive days followed by 2-4 days of interruption. In another embodiment the pharmaceutical composition is administered for 1-3 consecutive days, followed by 1-2 days of interruption.

In one embodiment of the method the dose of N-acetyl-L-cysteine is between 30 and 60 mg/kg/day on administration days. In another embodiment of the method the dose of N-acetyl-L-cysteine is between 30 and 45 mg/kg/day on administration days.

In one embodiment the method is for treating pain caused by endometriosis. In other embodiments the method is for treating infertility caused by endometriosis, for pre-treating mammals having endometriosis before laparoscopy or surgery or for treatment after laparoscopy or surgery, to prevent recurrences of endometriotic lesions.

BRIEF DESCRIPTION OF THE FIGURES

The invention will be explained in more detail in the following description, referring to the enclosed figures, where:

FIG. 7 reports the results of a preliminary clinical study performed on a total of 64 women, 33 treated by NAC and 31 untreated controls. The modification in size of cysts after three months of NAC treatment was measured by ultrasound as the maximum diameter.

DETAILED DESCRIPTION OF THE INVENTION

NAC in General

N-acetyl-L-cysteine (NAC) is a well known low molecular weight pharmaceutical drug, with the chemical formula:

NAC

The features of NAC are mainly related to its thiol group, which makes it effective in most biochemical pathways were the tripeptide gluthation (GSH), present in all human tissues at relatively high concentrations, even above 10 mM, acts. Cysteine is indeed among the three aminoacids composing GSH, so NAC is considered a precursor of GSH with its de-acetylated cysteine. NAC has been and still is largely used as a mucolytic agent, where the mode of action is generally attributed to the redox breakage of sensitive cysteine disulfur bridges in the mucus proteins. In fact NAC participates to the complex redox cycling of thiol groups, where several enzymes act. Indeed, of extreme physiological importance is the disulfide formation and breakage cycle, a common mechanism by which protein activity and cellular signaling is regulated. Enzymes such as protein tyrosine phosphatases and tyrosine kinases, for example, play pivotal roles in the control of the cell cycle, cell proliferation and differentiation, and many of them are regulated by the redox state of their cysteines.

Overall, although detailed mechanisms of action have not been finally elucidated, NAC appears to act in all biochemical pathways where GSH does. Enzymes and proteins whose activity is modulated by GSH operate is several processes either directly or through a net of signals transduction pathways. In this picture, NAC may either parallel GSH action, or may be even more effective than GSH.

GSH is e.g. normally conjugated to reactive metabolites formed by paracetamol and helps detoxify them. When paracetamol is overdosed GSH is however depleted and the paracetamol metabolites start reacting with cellular proteins, eventually leading to cell death. In the treatment of fulminant hepatic failure after paracetamol poisoning NAC acts instead of GSH in the detoxification of paracetamol metabolites. NAC is believed to be virtually absent of undesired side effect, which is also indicated by the high NAC doses that are used in the treatment of paracetamol poisoning, estimated, for a 70 kg individual, of about 40 g/day.

Contrary to the tripeptide GSH, which can be degraded already in stomach, the simple NAC molecule freely diffuses in almost all tissues and cells. NAC pharmacokinetic studies determined a peak concentration in plasma reached in about one hour, with a half-life of about three hours. Total clearance occurs between six and twelve hours.

NAC as an Antiproliferative, Differentiating Agent

The inventors have recently found that N-acetyl-L-cysteine (NAC) possesses a marked antiproliferative effect on cancer cells of epithelial origin—the same origin as of endometrial cells (Cell Death and Differentiation 2005, 12(10): 1285-1296). Although cancer and endometriosis are principally unrelated diseases they share some common properties which eventually led the inventors to the idea that NAC might also be useful in the treatment of endometriosis. In particular, endometriosis, just like cancer, is a proliferative disease albeit with other unknown underlying molecular mechanism and aetiology. The observations made in cancer will here be presented as a background to the effects of NAC and as a likely mode of action also in endometriosis.

NAC was used to arrest proliferation and induce differentiation in two adenocarcinoma cell lines and in primary normal keratinocyte cells, all of epithelial origin. In these systems, the differentiation was characterized morphologically, biochemically and through gene expression analysis (the gene expression analysis extensively reported in BMC Cancer 2005, 5: 75).

The antiproliferative effect of NAC, in the study of cancer, was not related to cell death or to toxicity but, instead, was due to the activation of a physiological differentiation pathway, which can be regarded as a normalization of cell functions towards the tissue of origin.

In addition to the decreased proliferation, the morphology of NAC-treated cancer cells was also altered. In vitro, epithelial cells under active proliferation display an irregular morphology—a mesenchymal morphology—and often form several multiple cell layers. On the contrary, when cells undergo a differentiation process, toward the structure and function of their final target tissue, they stop proliferation, their morphology becomes regularly polygonal, each cell sometimes thicker, and they form a single layer of adjacent cells. This process is accompanied by increased cell-cell and cell-substratum junctions, consistent with a shift from a proliferating mesenchymal to an adhesive, less motile and differentiated phenotype.

Figure 6:
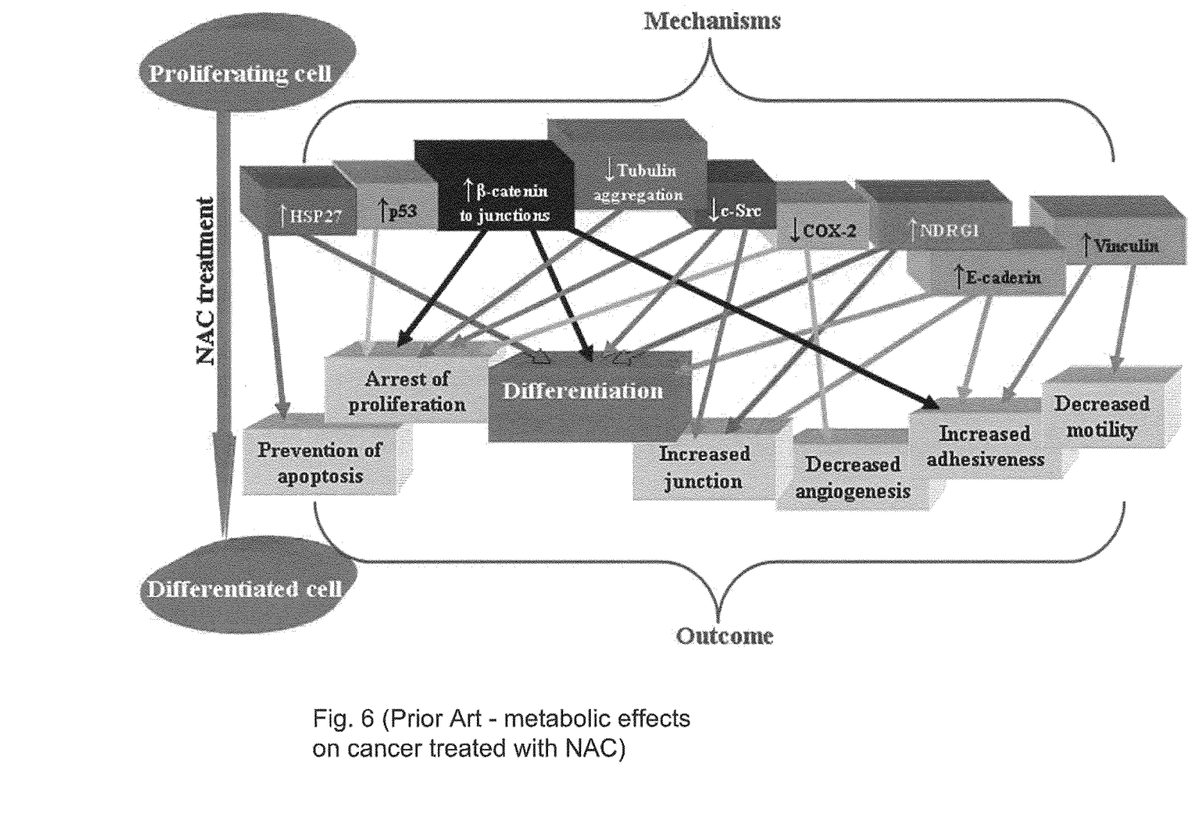
FIG. 6 is a schematic representation of prior art, showing several mechanisms operating when proliferating cells, as exemplified by cancer cells, are treated by NAC. These mechanisms converge into cell terminal differentiation. The examples of the present disclosure also show that at least some of these effects also occur when NAC, according to the present invention, is used to treat endometriosis.

On a whole, a complex series of metabolic changes were detected after NAC supplementation to cancer cells, all converging in arresting the uncontrolled proliferation and in inducing their terminal differentiation, as depicted in the scheme shown in FIG. 6.

Notably, NAC treatment induced a considerable increase in cell-cell and cell-substratum adhesion complexes. Uncontrolled proliferation can be regarded to as a condition where cells have lost the contact inhibition and their ability to respond to differentiation signals. Cells entering the differentiation pathway exhibit a noticeable increase in cell-cell junction complexes, and the process is also generally indicated as contact inhibition. Several evidences indicate that signals for the cells to enter the differentiation end-point originate from the components of cell-cell complexes themselves. These junctions are also a way for the diffusion of signals between cells.

Migrating cells such as endometrial cells in endometriosis, must in addition to a decreased amount of adhesion complexes, possess and secrete enough active matrix metalloproteinases, enzymes devoted to the degradation of the extracellular matrix, to enable migration through the extracellular matrix. Interestingly, in this model of epithelial cancers, NAC was found to down-regulate this enzyme, suggesting that cell migration was hindered. Also, example 1 of the present disclosure indeed shows that NAC, when used according to the present invention for the treatment of endometriosis, down-regulates the expression of matrix metalloproteinase 9 (MMP-9). This suggests that NAC might hinder cell migration both from eutopic endometrium to new implants (prevention of recurrences) and in endometriotic tissue (prevention of further lesions).

A known effect of NAC is also related to its anti-inflammatory effect, a reason for its addition to the family of nonsteroidal anti-inflammatory drugs (NSAIDs). The gene expression profile of NAC-treated cells showed, indeed, a down-regulation of cyclooxygenase-2 (COX-2), a gene whose induction is associated with inflammatory reactions. Also this effect of NAC was confirmed in endometriotic tissue in example 1 of the present disclosure, suggesting that NAC may also relieve the symptoms related to inflammation in endometriosis. As an example of the ability of NAC to modulate signal transduction in cells through the redox status of sensitive cysteines, the enzyme non-receptor tyrosine kinase c-Src was studied in an in vitro model of colon carcinoma (CaCo-2) cells and ovary carcinoma (OVCAR-3) cells (Free Radicals Biology and Medicine 2008, 45(11): 1566-72). c-Sre is involved in the proliferation/differentiation switch, and is active in the assembly/disassembly of junctional complexes and of the cytoskeletal organization. This kinase is activated and over-expressed in a number of human cancers, particularly in colon and ovary carcinoma. Conspicuous international drug design efforts are indeed devoted to the search of specific c-Src inhibitors. Instead, it was found that a simple treatment of adenocarcinoma cells with NAC can reach the objective of c-Src inhibition, with a mechanism related to redox transitions in sensitive cysteine residues in c-Src, able to switch off this kinase and to deliver it to endolysosomes, where it is stored or degraded. Thus, the NAC induced terminal differentiation in adenocarcinoma cells was related to the inhibition of c-Src. Of note, the activity of this kinase appears of relevance during the decidual phase of endometrial cells cycling, thus suggesting the involvement of its de-regulation in endometriosis (Endocrine Journal, 2008, 55(5): 795-810).

NAC and Endometriosis.

As explained in the background section it has previously been proposed that NAC could be used in new therapeutic strategies for endometriosis, based on its use as an antioxidant and a ROS scavenger. From the epithelial cancer studies described above the inventors of the present invention noticed that NAC had some advantageous effects, other than those as an antioxidant and a ROS scavenger, on epithelial cancer cells and that those effects could also be useful in the treatment of endometriotic cells, if the endometriotic cells should respond similarly. In particular, it was hoped that the anti-proliferative and differentiating effects of NAC seen in cancer would also occur when NAC was used in the treatment of endometriosis.

It was believed that if NAC had the following molecular effects, which had been observed in cancer, also on endometriotic tissue they would be beneficial for the treatment of endometriosis;
  i) an increase in cell-cell and cell-substratum junctions, consistent with a shift from a proliferating to a differentiated phenotype;
  ii) a decrease in the expression of matrix metalloproteinases, associated with a decrease in cell migration;
  iii) a decrease in the expression of cyclooxygenase-2 (COX-2), associated with a decreased inflammatory reaction;
  iv) a modulation of c-Src activity to regulate endometrial proliferation/deicidualization cycle and to allow pregnancy.

Hence, it was hypothesized that NAC might have the following physiological effects on endometriosis:
  i) a decrease in endometrial cell proliferation;
  ii) a reduction of local chronic inflammation, and thus a related pain relief;
  iii) a normalization to the tissue of origin, the eutopic endometrium, through a more regular proliferation-differentiation cycling;
  iv) a decreased number of ectopic endometrial cells related to decreased cell motility due both to the reduction in tissue metalloproteinases and to the increased cell-cell and cell-substratum junctions;
  v) a reorganization of the conformation of estrogen receptors through a reassembling of disulfide bridges in relevant cysteine residues.

On a whole, the hypothesized outcomes were all verified either directly or indirectly through the patients' response in a clinical study and through histological analysis of their biopsies or, in an animal model, at the level of morphology, histology, biochemistry and molecular biology.

In particular, the inventors have found that NAC indeed reduces the expression of cyclooxygenase-2 (COX-2) and matrix metalloproteinase 9 (MMP-9) in endometriotic tissue. They also show that NAC induces the re-localization of E-cadherin from the cytoplasm in endometriotic tissue, to cell-cell junctions in NAC treated tissue. This indicates an increase in cell-cell junctions, which is consistent with a decrease in cell proliferation. Indeed, other effects, such as the increased expression of p21 and the decreased expression of Ki-67, also indicate that NAC treatment in endometriosis leads to decreased cell proliferation. The inventors also show that these molecular effects of NAC treatment of endometriosis lead to a reduction in the size of endometriotic lesions, to pain relief and to desired pregnancy. An advantage with using NAC to treat endometriosis or indications related to endometriosis is that the normally used hormone treatments for endometriosis, which suppress ovary function, do not need to be used. The use of NAC thus, in comparison, increases the likelihood of these patients to get pregnant. NAC treatment before surgery also resulted in more regular and compact endometriomas which were more easily removed and led to extremely low bleeding during laparoscopy.

Dosage Regimen

From the study of NAC treatment on adenocarcinoma cell lines and primary normal keratinocyte cells (Cell Death and Differentiation 2005, 12(10): 1285-1296), it was concluded that the effective dose of NAC for induction of the antiproliferative-differentiating effect varied and was cell type dependent. The tissue of origin thus dictates the effective NAC concentration required to observe a complete block of proliferation, and has to be determined for each tissue. In addition, the dose of NAC was also related to the cell malignancy. In detail, while normal cells required a low dose to stop proliferating and start differentiating, carcinoma cells with characteristic poorer prognosis required a higher NAC concentration.

For the purpose of the present invention a dosage regimen of NAC for the treatment of endometriosis in a mammal, including human, was developed based on the following criteria:
1) a dosage of NAC per day which is in agreement with other current clinical treatments and is considered without undesirable side effects;
2) a dose which is considered high enough to fulfill the requirement of abnormally proliferating cells, to switch them into the differentiation pathway;
3) given a reported decrease in NAC plasma level after prolonged treatments (Pendyala L, Creaven P J. Cancer Epidemiol Biomarkers Prev. 1995; 4:245-51), the suspension of the treatment for about half of each week was considered for an optimal biological response in a treatment for two months or longer.

The composition of the present invention, comprising NAC for the treatment of endometriosis or indications associated with endometriosis is according to one embodiment to be administered at a dose between approximately 20 and 90 mg/kg/day. The lower limit is based on twice the dose used for mucolytic action, i.e. it is per se known to have a physiological effect. The upper limit is based on the consideration that higher doses have been found to cause gastric problems in many patients. In another embodiment of the present invention the composition comprises NAC to be administered at a dose of approximately 30-60 mg/kg/day. The lower limit has been shown to be effective in endometriosis and the higher limit is known to have virtually no side effects. In still another embodiment of the present invention the composition comprises NAC to be administered at a dose of approximately 30-45 mg/kg/day. This low dosage has surprisingly been shown to be effective in endometriosis.

In one embodiment the composition is to be administered for a period of time which is two months or more, or preferably three months or more. To counteract a decrease in NAC plasma level after prolonged treatment NAC may be administered at the prescribed dosage in an intermittent fashion, i.e. intermittent dosage regimen/treatment. By intermittent administration or treatment is meant that the treatment is interrupted in periods, i.e. that the pharmaceutical composition is administered for a period of time, e.g. a few days, followed by an interruption in administration, where no pharmaceutical composition is administered for a period of time, e.g. for a few days. Intermittent treatment can be regular, e.g. treatment for a fixed number of days or weeks, followed by interruption for a fixed number of days or weeks. Examples include repeated schemes with treatment for 4 days followed by interruption for 3 days each week or treatment for 2 weeks followed by interruption 1 week. A special case of regular intermittent treatment is pulsed treatment, i.e. with regular treatment and interruption duration, e.g. administration every other day or administration for two days followed by two days of interruption etc. Irregular intermittent treatment schemes that are not regularly repeated or have a more complex scheme that is repeated is also conceivable, e.g. dependent on response to treatment. In different exemplifying embodiments of the present invention the prescribed dose of NAC is administered for 3-5 consecutive days followed by 2-4 days of interruption, or administered for 1-3 consecutive days followed by 1-2 days of interruption.

In one embodiment, by referring to a body weight of approximately 60 kg, the NAC dose is in the range between 1.2 and 5.4 g/day, preferably between 1.8 and 3.6 g/day. The dose may be divided in two or more, preferably three or four, daily administrations of either one or two doses (e.g. pills) each, where each dose may comprise e.g. 0.15-2.7 g of NAC or preferably 0.6-1.2 g of NAC. The treatment includes the administration of the above mentioned doses pulsed or intermittently, e.g. every other day or for three to four consecutive days each week, with a suspension from four to three days, respectively. The minimum total duration of the treatment is of two months, with no maximum duration. For patients with other weights, e.g. over- or underweight persons the daily dose needs to be adjusted accordingly.

In one embodiment of the present invention the pharmaceutical composition for treatment of endometriosis or endometriosis related symptoms comprises NAC in a dose of 150-5400 mg to be administered in two or more administrations per day, for a period of at least 2 months, such as at least 3 months. In a preferred embodiment of the present invention the pharmaceutical composition comprises NAC in a dose of 230-3600 mg to be administered in two or more administrations per day, for a period of at least 2 months, such as at least 3 months. The treatment includes the administration of the above mentioned doses pulsed or intermittently, e.g. every other day or for three to four consecutive days each week, with a suspension from four to three days, respectively.

Pharmaceutical Formulations

A pharmaceutical composition according to the present invention may be prepared in a manner per se known by a person skilled in the pharmaceutical art. The composition may comprise an effective amount of NAC, in accordance with the invention, as well as a suitable carrier or excipient that serves as a vehicle or medium for the active ingredient. Such carriers or excipients are known in the art and include solid materials such as citric acid, natrium citrate, natrium (acid) carbonate plus flavoring. The pharmaceutical composition is preferably adapted for oral administration. Such compositions could be administered in different forms, at present preferably as tablets. Other forms, such as capsules, suppositories, solutions, suspensions, syrups or the like are also conceivable.

The invention requires a strict assessment of the pharmaceutical quality of NAC preparation for obtaining the effective dose. Therefore, brand or certified generic preparations have to be used. NAC is not a stable molecule, its active thiol residue can be easily oxidized by oxygen, light and other radiations, so that the effective dose would not be reached. The preparation is thus preferably protected from light, in soluble tablets, with sodium hydrogen carbonate, which helps in a partial removal of oxygen from water during dissolution.

It has been observed that high doses of NAC may cause abdominal pain. For overcoming this, an option is to provide NAC in a formulation with gastric protection, suitable for preventing NAC release/solubility in the stomach. Such formulations are well known in the art and may be used with the present invention. For example, tablet coatings that are resistant to gastric fluids and allow release of the drug only in the intestine, after its transit through the stomach, may be used. Commonly used formulations include polymers such as cellulose derivatives, methacrylate amino ester copolymers. The coating protects the tablet core from disintegration in the acidic environment of the stomach by employing pH sensitive polymer, which swell or solubilise after having passed through the stomach, in response to an increase in pH, to release the drug. Another option is to lower the dose of NAC entering the blood stream at any one time.

Administration of NAC three or more times daily can be difficult to accomplish for the patient. Nevertheless, a repeated administration can be desirable to achieve a nearly constant serum concentration of NAC. To overcome these problems, a once or twice-a-day administration could be easier to handle for the patient, for instance morning and night. One option is to provide NAC in a slow-release formulation (also denoted sustained-release or controlled-release). By being able to reduce the rate of diffusion and uptake of NAC into the blood stream such a formulation enables administration of a larger dose at longer intervals. The dose is then distributed in the blood over a long time in small quantities, e.g. over 12+12 hours in the case of a twice-a-day regimen scheme. Many different technologies and formulations for slow-release are since long known in the art and may be applied with the present invention. In such technologies the active substance is for example encapsulated in a coating or matrix that is insoluble or less soluble in the body fluid where it is administered.

Formulations having a combined effect of slow-release and gastric protection is also possible and may be used within the present invention.

Use/Medical Indications of the Present Invention

The present invention has been shown to have beneficial properties in many aspects related to endometriosis and may be used both for the treatment of endometriosis and for treatment of various indications associated with endometriosis. By treatment of various indications associated with endometriosis is meant e.g. treatment to ease the symptoms of the disease such as pain and inflammation; treatment to increase the likelihood of getting pregnant; pre-treatment before surgery to ease the removal of endometriotic lesions and to improve the outcome of surgery; treatment after surgery to prevent the recurrence of lesions; and preventive treatment in case of validated, assessed risk factors or presence of familial endometriosis.

NAC, according to the present invention, has been shown to decrease lesion size and to revert proliferative tissue to more differentiated, normal tissue. Thus, in one embodiment of the present invention the pharmaceutical composition comprises NAC for the treatment of endometriosis in order to reduce—eventually up to their disappearance—endometriomas, adhesions, peritoneal implants and deep lesions located in the recto-vaginal septum or in other sites.

NAC, according to the present invention, has also been shown to relieve the symptoms of pain caused by endometriosis. Thus, in another embodiment of the present invention the pharmaceutical composition comprises NAC to relieve pain associated with endometriosis. In another embodiment of the present invention the pharmaceutical composition comprises NAC for the promotion of a desired pregnancy in a person with endometriosis.

In still another embodiment of the present invention the pharmaceutical composition comprises NAC for pretreatment of laparoscopy or surgery in cases of endometriosis, to facilitate the mass removal, decrease bleeding, make tissues more compact/less fragile. In another embodiment of the present invention the pharmaceutical composition comprises NAC for the prevention of recurrences after laparoscopy or surgery. In still another embodiment of the present invention the pharmaceutical composition comprises NAC for the use in case of validated, assessed risk factors, for prevention of endometriosis due to familial incidence.

EXAMPLES

The invention will now be further described and illustrated by reference to the following examples. It should be noted, however, that these examples should not be considered as limiting the invention in any way.

Example 1

Effect of NAC in a Murine Model of Endometriosis

Materials and Methods
Materials.
Unless specified, all chemicals were from Sigma-Aldrich, Milan, Italy.
Animals.
36 female, 6 to 8 weeks-old BALB/C mice were purchased from Charles River Italia (Calco, Italy). Pellet food (enriched standard diet; Mucedola, Milan, Italy) and water were provided ad libitum. Animals were kept on a light/dark cycle of 16/8 hours under controlled conditions. Prior to any invasive procedure, the mice were anaesthetized by intraperitoneal injection of 0.4 ml of a physiological solution containing 2.5% AVERTIN.
Induction of Endometriosis.
Induction of endometriosis was performed following the method described in Somigliana et al, Hum Reprod 1999 December; 14(12):2944-50. Surgical interventions were performed under clean conditions. Briefly, uterine horns of syngenic mice were removed through a small midline incision into the peritoneal space, just below the umbilicus, and put into a Petri dish containing phosphate-buffered saline (PBS). Endometrial fragments were obtained by finely chopping uterine horns by using a razor blade. Fragments were suspended in 0.6 ml of PBS and rapidly inoculated into the peritoneal cavity of recipient mice with a ratio of one donor to two recipients. The endometriosis-induced mice were randomly divided into two groups of 12 mice each: control and NAC-treatment.
NAC Treatment.
The day after the endometrial implant, mice of the treatment group were subjected to gavage with 100 [mu] [iota] of the 10 mg/ml stock solution of NAC in water. The control group only received water. NAC administration was continued daily for 21 days. Given the average mouse body weight of 22.5+−0.7, the NAC dose of 1 mg/mouse corresponds to 44 mg/kg/day. No evidence of toxicity was noted at the administered dose based on body weight—unchanged at the end of treatment—food consumption, grooming behavior, or activity levels compared with controls. At the end of treatment, mice were killed through cervical dislocation.
Collection of Endometriomas.
At the end of the treatment, animals were sacrificed and endometriotic lesions were carefully excised from the surrounding tissue, their total weight and number was assessed. Cysts were either immediately fixed in 10% formalin or frozen in liquid nitrogen and stored at −80 [deg.] C.
Histology and Immunohistochemistry.
Formalin-fixed samples were paraffin-embedded and tissue sections (5 [mu] [iota] [eta] thick) were stained using haematoxylin-eosin. All slides were evaluated by an experienced pathologist who was blind to the study and the histological diagnosis of endometriosis was based on the morphological identification of endometrial glandular tissue and stroma.
For immunohistochemistry, sections were deparaffinized and rehydrated in graded ethanol. For antigen retrieval, sections were microwaved for 6 min in 0.1 M citrate buffer (pH 6.0) and endogenous peroxidase activity was blocked by a 20 min incubation in 3% H2O2/methanol. Sections were rinsed in PBS/TritonX-100, immersed for 15 min in PBS-bovine serum albumin (BSA) 1% to block unspecific binding sites, and then incubated with the selected primary antibody diluted in PBS-BSA 1%. For the immunodetection of cyclooxygenase (COX)-2 (Rabbit anti-mouse polyclonal, Cayman Chemical, Milan, Italy), Ki-67 (Rabbit anti-human polyclonal, Monosan Xtra, DBA Italia, Segrate, Italy), and E-cadherin (BD Biosciences, Milan, Italy), incubation was performed overnight at 4 [deg.] C. and the dilutions were 1:100, 1:600, 1:200, respectively. Immunohistochemical staining was continued using the DAKO Cytomation LSAB2 System-HRP (Dako Italia, Milan, Italy) and the antibody binding sites were visualized by strept Rabbit anti-human polyclonal, avidin-biotin peroxidase complex solution using diaminobenzidine as a chromogen. Sections were counterstained with haematoxylin, dehydrated, mounted in Canada balsam and then observed with a Leica microscope. The quantification of Ki-67 expression was carried out in a blind fashion by two independent observers; each observer counted at least 200 cells in more than 10 randomly chosen fields for each sample and the Ki-67 labeling index was expressed in percentage.

RNA Extraction, Semi-Quantitative RT-PCR and qRT-PCR.

Total RNA was isolated by lysing the frozen endometrial cysts with TissueLyser (QIAGEN, Milan, Italy) using TRIzol Reagent (Invitrogen, Milan, Italy) according to the manufacturer's instructions. One microgram of total RNA from each sample was treated with 1 U of DNAse I (Invitrogen) and reverse transcribed with 200 U of Superscript III Reverse Transcriptase (Invitrogen), using 250 ng of random primers in 20 [mu] l of final volume. The same cDNA product obtained from each sample was used for subsequent PCR amplification with the primer sets prepared for the target genes. 18S RNA housekeeping gene was used as the internal control. Negative control samples consisted of reaction mix and primers without cDNA template. Primer sequences (Table I) were designed using the software Primer-BLAST available online from: http://www.ncbi.nlm.nih.gov/1

First, the ratio between the sample and the housekeeping gene was calculated by simultaneous amplification of gene-specific mRNA and 18S RNA in a single reaction tube. Since this procedure was not successful for all samples—likely due to the relative small number of specific transcripts thus of a preferential amplification of 18S mRNA—to prevent quantitative inaccuracies deriving from competitive effects, the target genes and 18 S cDNA generated in the same RT reaction were amplified in separate tubes. To document amplification in the exponential range, an amplification plot for 18S RNA was generated and the appropriate number of cycles was selected. Semi quantitative PCR was performed in a 25 [mu] [iota] reaction volume, with 1 [mu] [iota] of cDNA, 2 mM MgCl2, 0.2 mM dNTPs, 0.5 [mu] [Mu] of each primer and 1.25 U of Hotstart Taq Polymerase (QIAGEN). The PCR amplification was performed by iCycler (Bio-Rad, Milan, Italy). PCR products were then resolved electrophoretically on 1.5% agarose gel and stained with ethidium bromide. The levels of target mRNA were estimated by densitometric scanning and normalized against 18S loading controls. The densitometric analyses of the PCR products were performed using an image software Quantity One (VersaDOC, Bio-Rad).

TABLE I

Primers sequences used for semi quantitative and qRT-PCR

| Target mRNA | primers | Sequence | Annealing (per 30 sec) | N. of cycles | PCR Product (bp) |
|---|---|---|---|---|---|
| 18 S RNA NR_003278 | forward reverse | CGCGGTTCTATTTTGTTGGT AGTCGGCATCGTTTATGGTC | 60° C. | 18-24 | 219 |
| COX-2 NM_011198.3 | forward reverse | CCCCCACAGTCAAAGACACT AGTTGCTCATCACCCCACTC | 60° C. | 35 | 196 |
| MMP-9 NM_013599.2 | forward reverse | TGAATCAGCTGGCTTTTGTG GTGGATAGCTCGGTGGTGTT | 60° C. | 35 | 242 |
| P21 (cdkn1a) NM_007669.4 | forward reverse | TCCACAGCGATATCCAGACA ACGAAGTCAAAGTTCCACCG | 60° C. | 35 | 196 |

Results

Effect of NAC Treatment on the Growth of Endometriotic Lesions.

Figure 1:
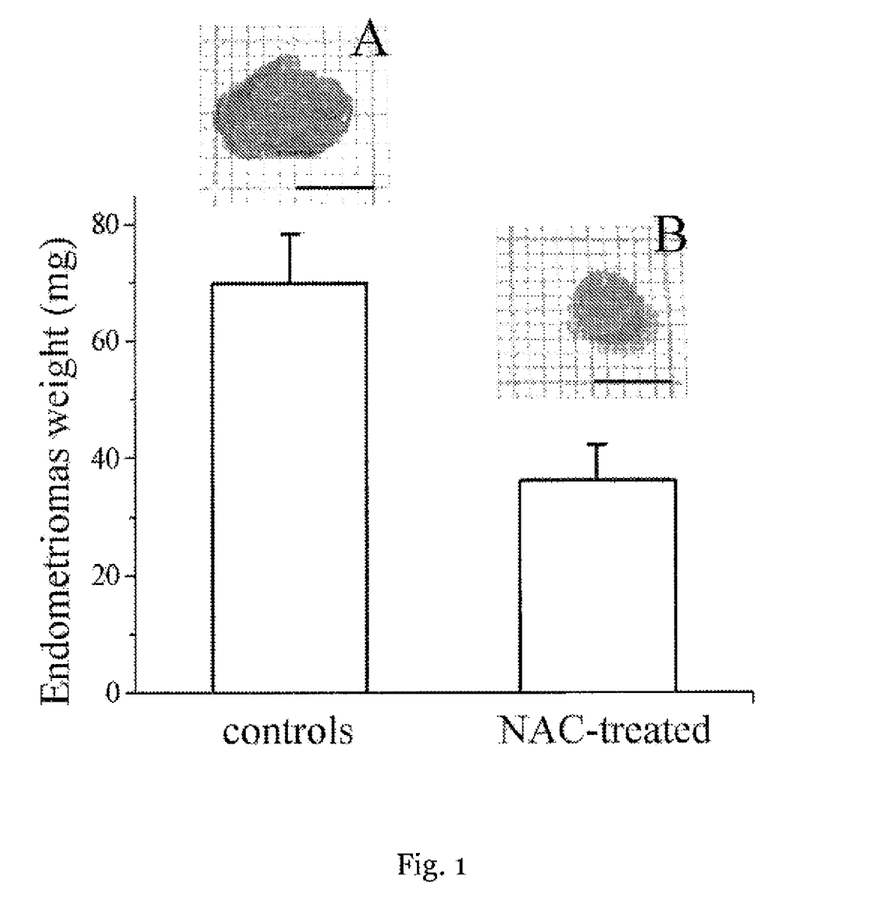
FIG. 1 shows the inhibitory effect of NAC on the growth of the endometriotic lesions in mice, as demonstrated by example 1. Average total weight per control (n=10) and NAC-treated (n=10) animals, after 21 days from implant, with standard error. Significance p<0.05. In the insets above histograms, representative pictures of endometriomas are reproduced for a control (A) and a NAC-treated (B) case. Bar: 1 cm.

Twenty-one days after the induction of endometriosis, all experimental mice were sacrificed and their endometriomas removed and collected. Of the 12 control mice, one died and one did not develop endometriomas. Of the 12 mice treated with NAC two did not develop endometriomas. Morphologically, ectopic lesions were large, cystic and vascularized: they consisted of fluid-filled cysts, which were either white, red or occasionally brown in color, and preferentially localized on the peritoneum of abdominopelvic cavity. In the insets of FIG. 1.1, we report representative pictures of cysts from control (A) and NAC-treated (B) animals. On average, a significant weight reduction was observed in the treated group (n=10) compared with the controls (n=10) (FIG. 1).

NAC Reduces COX-2 and MMP-9 Expression, and Switches Off Proliferation.

Figure 2A:
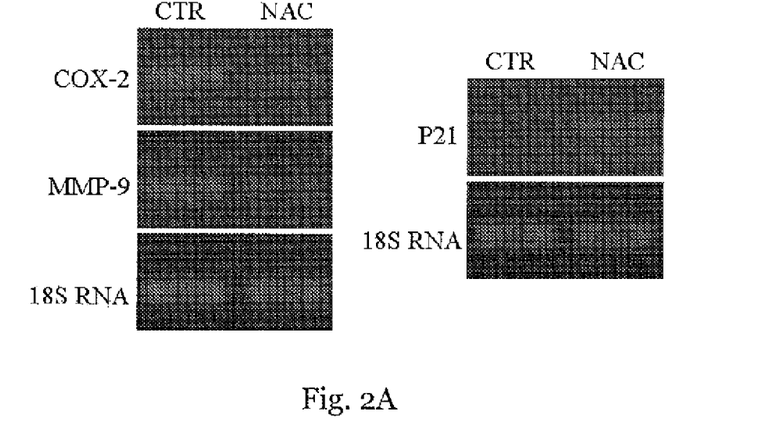
FIG. 2A shows representative gels of semi-quantitative RT-PCR, as demonstrated by example 1.
Figure 2B:
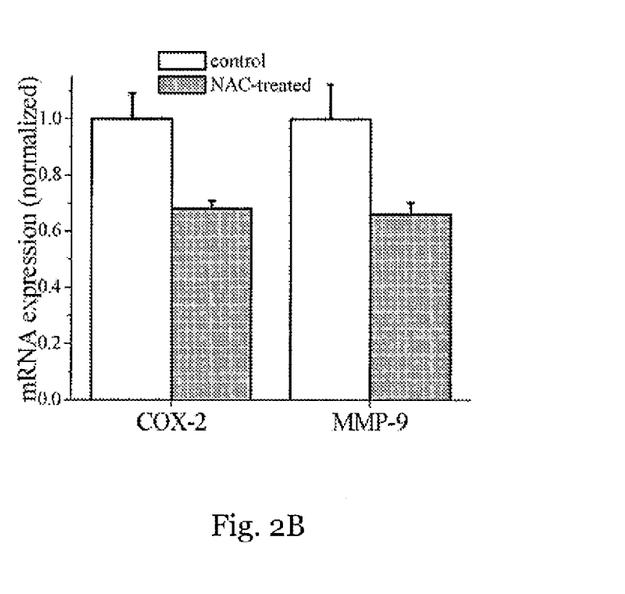
FIG. 2B shows decreased expression of COX-2 and MMP-9 in cysts from NAC-treated mice, as demonstrated by example 1. Semi-quantitative RT-PCR values, averaged over 5 control and 5 NAC-treated mice, with standard error.

The RT-PCR analysis revealed that, relatively to cysts from control mice (n=5), NAC treatment (n=5) induced a significant reduction in the levels of COX-2 (−32%) and of MMP-9 (−34%) mRNA, with a significance p<0.01, as normalized to the 18S expression (FIGS. 2A and B). The P21 gene, typically expressed only when the proliferation cycle is blocked, was never expressed in the 5 controls, while it was expressed in 3 of the 5 examined NAC-treated samples (representative example in FIG. 2A).

NAC Drives E-Cadherin Relocalization.

Figure 3:
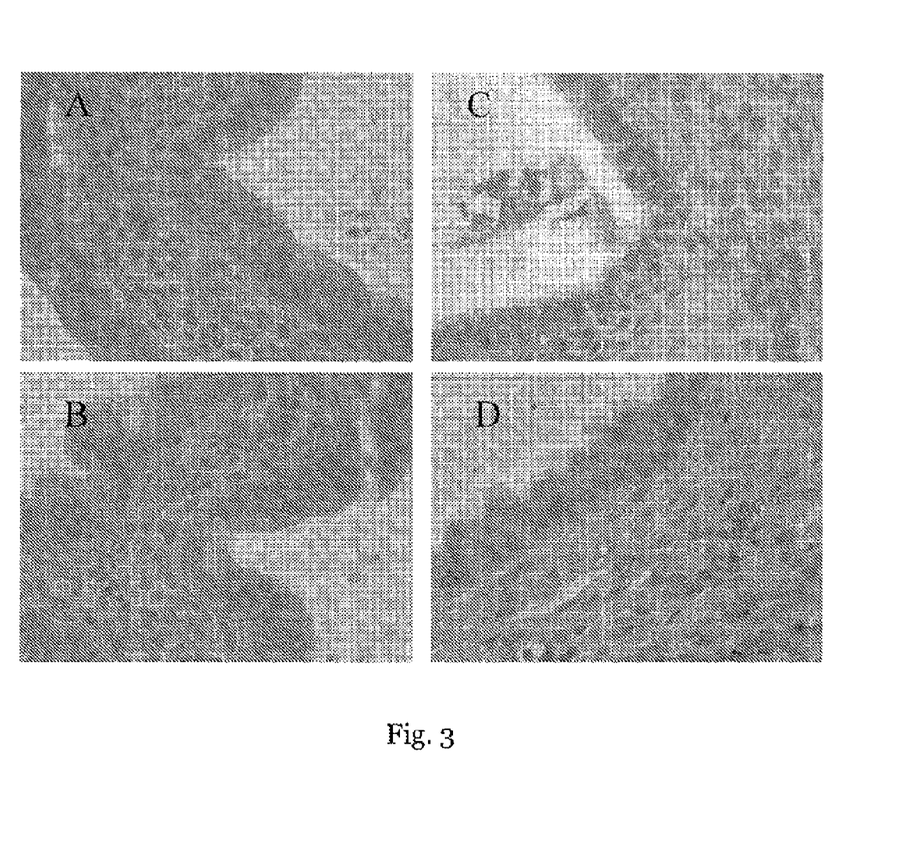
FIG. 3 shows relocation of E-cadherin in cysts from NAC-treated mice, as demonstrated by example 1. Representative images of E-cadherin immunostaining in endometriomas from controls (A and B) and NAC-treated mice (C and D). In control samples, a diffuse brownish staining can be observed in the whole cytoplasm of epithelial cells, while in NAC-treated samples this staining is well confined at the level of cell-cell contacts. Original magnification 40×.

Immunohistochemical detection of E-cadherin was positive in 100% of examined cases. Labeling was restricted to glandular epithelial cells while none of the sample presented stromal staining. At a cellular level, in cysts from control mice we found that E-cadherin staining was diffused all over cell cytoplasm, whereas in cysts from NAC-treated mice E-cadherin was mainly detected along cell-cell junctions (FIG. 3). E-cadherin is part of the multiprotein adhesion complex, therefore its increased presence at the cell borders indicates an increase in cell-cell adhesions. In addition and in agreement with the P21 expression reported above, this relocation is consistent with the loss of cells' proliferating behavior switched towards terminal differentiation (Conacci-Sorrell et al, J. Clin. Invest. 2002, 109: 987-991; Parasassi et al, Cell Death Differ. 2005, 12: 1285-1296).

NAC Treatment Decreases the Amount of Cox-2 in Endometriomas.

Figure 4:
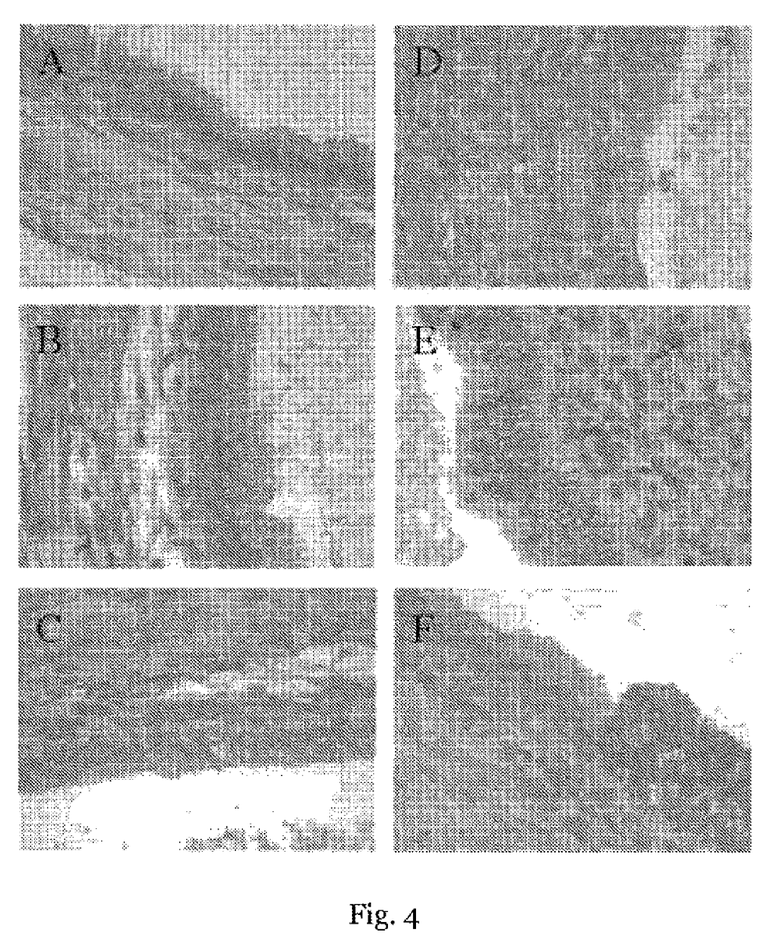
FIG. 4 shows decreased Cox-2 staining in cysts from NAC-treated animals, as demonstrated by example 1. Representative images of immunohistochemical staining of cysts from control mice (A-C) and from NAC-treated mice (D-F). In control samples, a conspicuous presence of brownish staining is detected in several areas, while this is barely detectable in NAC-treated samples. Original magnification 40×.

Immunohistochemical detection of the inflammation-related Cox-2 protein revealed that relatively to cysts from control mice, the samples collected from NAC-treated mice displayed quite a decreased staining, that, in some cases, was completely absent (FIG. 4).

NAC Decreases the Number of Proliferating Cells.

Figure 5:
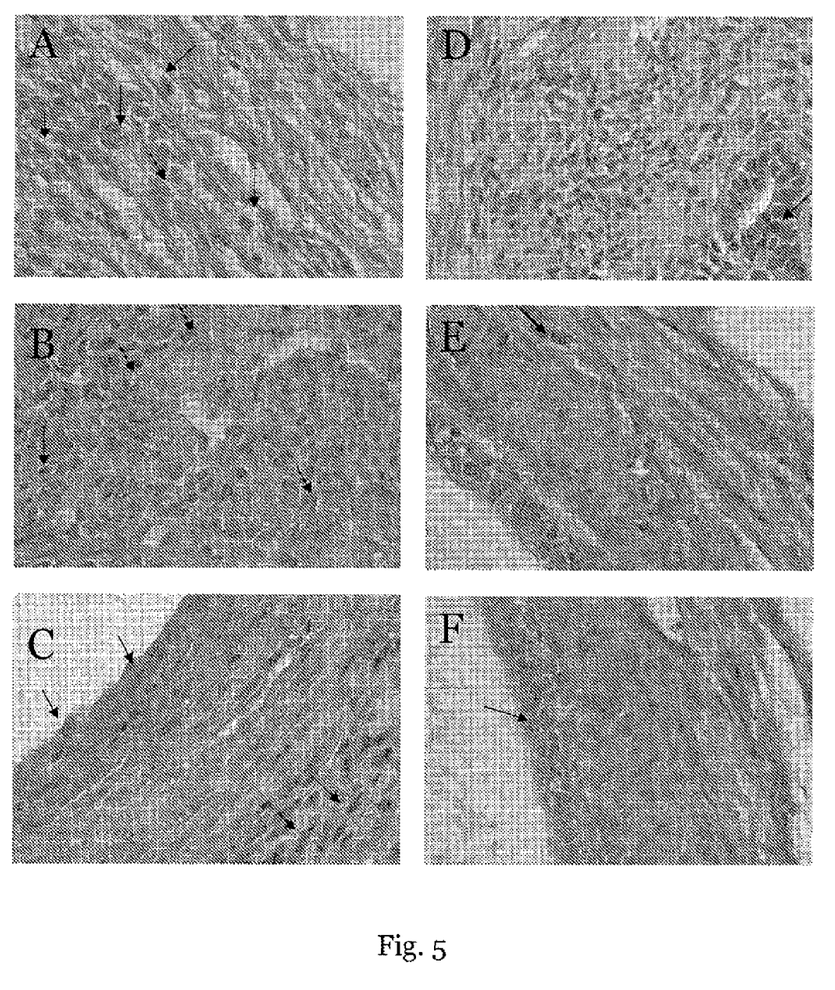
FIG. 5 shows decreased Ki-67 staining in cysts from NAC-treated animals, as demonstrated by example 1. Representative images of immunohistochemical staining of cysts from control mice (A-C) and from NAC-treated mice (D-F). Arrows point to stained, proliferating cells. Original magnification 40×.

The Ki-67 antigen (Ki-67) is a classic marker of cellular proliferation, with resting, non-cycling cells completely lacking Ki-67 expression. When used to stain cysts from control mice, several labeled cells could be detected (arrows in the panels A-C of FIG. 5). Instead very little labeled cells were detected in cysts from NAC-treated mice (arrows in D-F panels of FIG. 5). A statistical evaluation performed on 8 animals for each group (10 images/200 cells mouse) gave a reduction in proliferating cells of 54% (Table II).

TABLE II

Labeling index for Ki-67 with standard error. Significance: $p < 0.01$.

| Control (n = 8 × 5) | NAC-treated (n = 8 × 5) |
|---|---|
| 1.88 ± 0.28 | 0.87 ± 0.11 |

Discussion

The animal model of endometriosis was effective in inducing ectopic endometrial implants. Only one animal in the control and two in the NAC-treated group did not show endometriomas. Consistently with expectations, the weight—proportional to dimension—of cysts was lower in NAC-treated mice. This can be attributed to an antiproliferative effect of NAC (Parasassi et al, Cell Death Differ. 2005, 12: 1285-1296), as extensively illustrated here by the gene expression analysis and by immunohistochemistry. Indeed P21, a gene only expressed in differentiating, non-proliferating cells, was observed in 60% of NAC-treated animals while it was not expressed in controls. Conversely, the Ki-67 protein, which is only expressed in proliferating cells, showed a 54% decrease in NAC-treated relatively to control mice.

Proteins of relevance in endometriosis, such as the MMP-9 (Collette et al., Hum Reprod 2006; 21: 3059-3067) and Cox-2 (Carli et al, Endocrinology 2009; 150: 3128-3137), showed a decrease after NAC treatment. MMP-9 is considered fundamental for cell motion and invasive behavior, while Cox-2 is a paradigmatic enzyme associated to inflammation. Both relative genes showed a decrease of about 30% after NAC treatment. In addition, the amount of Cox-2 was also examined by histochemical staining in cysts and the results showed a relevant decrease in staining.

Based on the widely accepted notion considering cytoplasmic E-cadherin as a marker of proliferative cell behavior, while, on the opposite, its location at the cell-cell adhesion complex is considered both a marker and an inducer of differentiation, we also examined E-cadherin location in cysts from control and NAC-treated mice. The results are in a perfect agreement with our previous findings on adenocarcinoma cells (Parasassi et al., Cell Death Differ. 2005, 12: 1285-1296), showing a relocation of E-cadherin from cell cytoplasm to the cells borders after NAC treatment. This association of E-cadherin to adhesion complex is also in agreement with a less motile, less invasive cell behavior.

In conclusion, from all examined respects NAC can constitute an optimum treatment in endometriosis. When translated to the treatment of women, this drug has the relevant advantage of being virtually free of side effects, in comparison with the magnitude of undesired effects due to hormone treatment. NAC can therefore be used to reduce cyst dimension, to decrease local inflammation and the associated chronic pain, and to reduce recurrence after surgery. This last point is motivated by a decreased proliferation and decreased cell motility.

Example 2

Preliminary Clinical Study on the Effect of NAC to Treat Endometriosis

Aim of the Study.

This pilot clinical study was designed to treat women with endometriosis by using NAC instead of other treatments. The only possible additive treatment was with analgesics for pain relief, when needed.

Criteria for Patient Enrollment.

Women with a first diagnosis of endometriosis, based on pain and on ovarian ultrasound evidence of the disease, and patients with a recurrence of pain and/or ovarian endometrioma after laparoscopic treatment were enrolled in the study, Before treatment, the intensity of pain symptoms was measured by the means of a 10 points visual analogue scale (VAS) and the characteristics of the ovarian endometriomas by transvaginal ultrasounds. During NAC treatment, other treatments are excluded with the exception of analgesic to treat pain, when needed.

Patients.

From February 2008 to July 2010, 64 women diagnosed for ovaric endometriosis were enrolled in the study, with a mean age of 35+−7 years (+−SD). Of them, 33 were assigned to NAC treatment (mean age: 37+−6 years), while 31 did not follow NAC or any other treatment and were considered as control cases (mean age: 33+−8 years). All of them presented one or more cysts at one or both ovaries.

Treatment.

The prescribed NAC dose was close to that used in the animal study, of 30 mg/kg/day. In practice, for an average body weight of 60 kg, the prescription for all enrolled patients was of three oral doses of 600 mg NAC, three times a day, for three consecutive days each week, with four days of interruption. This resulted in 1.8 g of NAC per day, 5.4 g per week, 21.6 g per month. These precise modalities of treatment were based on the following considerations: 1) the dose of 1.8 g of NAC per day is in agreement with other current clinical treatments and is considered without undesirable side effects; 2) given NAC pharmacokinetics, the three daily doses of 0.6 mg approach a nearly constant plasma level, without discomfort of patients for a complex treatment; 3) given a reported decrease in NAC plasma level after prolonged treatments (Pendyala L, Creaven P J. Cancer Epidemiol Biomarkers Prev. 1995; 4:245-51), the suspension of the treatment for about half of each week warrants an optimal biological response in a lengthy treatment, e.g. two to six months or longer.

Follow-Up.

Pain symptoms intensity (VAS pain scale) and the size of the ovarian endometriomas (clinical and US exams) were evaluated after the first three months of treatment. If necessary, laparoscopic treatment was performed after 3 months.
Results Data after the first three-month follow-up period are reported below.

Figure 7A:
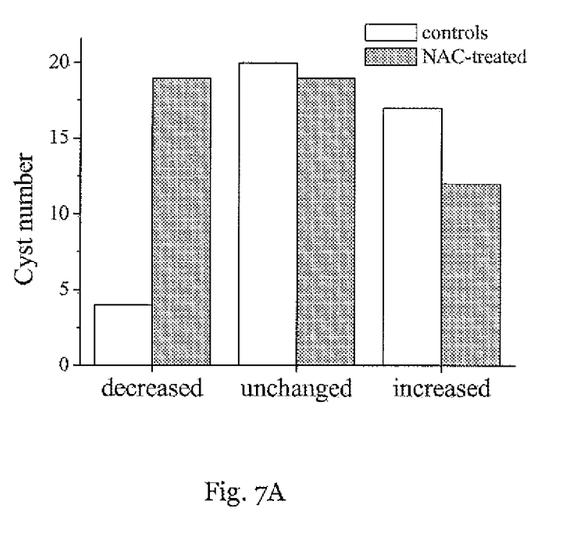
FIG. 7A shows the change in size of cysts in absolute numbers, in treated patients and controls.
Figure 7B:
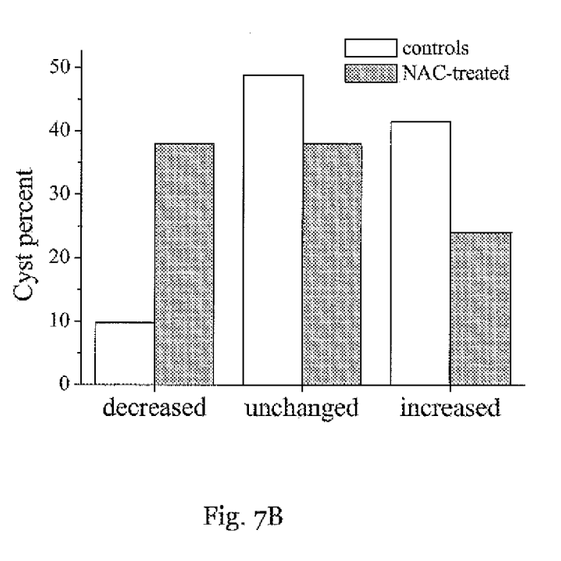
FIG. 7B shows the same comparison as a percent variation.

The modification in size of cysts (unchanged, increased or decreased) after three months of NAC treatment, as measured by ultrasound as the maximum diameter, is shown in FIG. 7A (absolute number of cysts) and FIG. 7B (percent cysts). The figures show a comparison of cysts in NAC treated patients and cysts in untreated controls. In percent terms (FIG. 7B), a decrease in cyst size was observed in 38% cases, while in controls only less that 10% cases showed a spontaneous decrease. Given the reduction of endometrioma size, several (21 out of 33) patients decided to cancel or postpone the programmed laparoscopy.

Pain perception was also modified after NAC treatment. Pain was evaluated, before and after the three-months treatment, by a 10-points visual analogue scale (VAS) with zero representing no pain and 10 representing the worst imaginable pain. Intensity of symptoms were classified as none (0), mild (1-4), moderate (5-7), or severe (8-10). NAC-treated patients reported an average pain reduction, from 7.6+−0.3 to 5.1+−0.8 ($p<0.01$) after three months of treatment.

No adverse side effects were reported.

Although we did not evaluate whether patients desired pregnancy, and therefore cannot attribute a statistical significance to our finding, we also report three cases of pregnancy, obviously not possible with the currently used therapies for endometriosis, targeting a suppression of ovary function.

Anecdotic was the observation, reported by an experienced surgeon, that at laparoscopy after NAC treatment, the endometrioma was more regular and compact and more easily removed, therefore associated with a relevant reduction in bleeding during laparoscopy.

In an additional case, a recto-vaginal septum nodule disappeared, suggesting NAC efficacy beyond ovaric endometriomas.

Example 3

Effects of Pulsed, Intermittent and Daily NAC Treatment on Experimentally Induced Endometriosis: Vaginal Hyperresponsiveness, as a Sign of Pain, in Rats—a Pilot Study Materials and Methods
Animals.

16 adult virgin female Sprague-Dawley rats were used. They weighed 200-230 g at the start of the study and were housed individually in a temperature-controlled room in plastic cages lined with bedding. The rats had ad libitum access to water and rat chow and were maintained on a 12-h light/dark cycle, with lights on at 07:00. Reproductive status (proestrus, estrus, metestrus, and diestrus) was determined by daily vaginal lavage performed.
Experimental Model and Pre-Surgical Training.

Prior to induction of endometriosis rats were trained to perform an escape response to terminate vaginal distention produced by an inflatable latex balloon. A small uninflated latex balloon was tied to a thin catheter lubricated before being inserted into the mid-vaginal canal. Inflating the balloon with different volumes of air distended the vaginal canal. The pressure produced by each volume of distention was control measured through a small-volume pressure transducer. The testing apparatus was a small cylindrical plexiglass chamber designed to contain the rat just enough to prevent her from turning around. An opening in the rear of the chamber allowed the catheter attached to the vaginal stimulator to be connected to a stimulus apparatus. A photosensor determined the position of the rat in the chamber. If the rat extended, as part of an escape response, the light beam was broken and the stimulus was terminated. The rats were adopted to the testing chamber by placing it in the chamber for 15 min daily for 5 days. The rats were then, during training sessions, accustomed to a mechanical escape response to deflate vaginal distention, which involved the rat extending her head to interrupt the light beam. All rats learned the escape response within 4 sessions. Once trained, testing sessions began.

Testing sessions were run 3 times/wk on non-consecutive days. Each testing session included a series of controlled escape trials. Each trial consisted of rapid inflation of the balloon (1 ml/s) to a fixed volume, where it remained until either the rat made an escape response or 15 seconds elapsed, and the balloon rapidly deflated. Different distention volumes, including a control volume (0.01 ml), were delivered three times each in random order. The maximum latency of 15 seconds was considered to be no response.

Time to response and escape responses were measured as a function of distention volume for each session, as described in Cason A M et al (Horm Behav. (2003), Vol. 44, pages 123-31). The shorter the time to response and the smaller the volume giving response, the greater the escape response in the rat. For each rat, the escape responses and pressures/volumes for all of that rat's sessions (at least 12 sessions) were combined, and the mean values calculated. In all four experimental groups (see below), baseline escape responses to vaginal distention prior to the endometriosis surgery was found to be very similar.
Induction of Endometriosis.

Endometriosis may be experimentally induced in rats by autotransplanting pieces of uterus. The endometriosis surgery was done following a protocol originally developed by Vernon and Wilson 1985 (Fertility and Sterility, 1985, Vol. 44, pages 684-694). Rats in diestrus were anesthetized, placed on heating pad to maintain body temperature and the surgery carried out. A midline abdominal incision was made to expose the uterus. Four pieces of uterine horn were sewn around alternate cascade mesenteric arteries that supply the caudal small intestine. Postoperative recovery was uneventful and regular estrous cyclicity resumed in all rats within one week.
NAC Treatment.

All rats were treated with NAC at a dose of 60 mg/kg/day (where applicable on days when administered) or placebo for 8 weeks after surgery. The rats were divided into four experimental groups:

A first group received pulsed NAC treatment, i.e. treatment every other day.

A second group received intermittent NAC treatment, i.e. daily treatment for 5 days and 2 days rest (i.e. 2 days without treatment).

A third group received daily NAC treatment.

A fourth group received sham treatment, i.e. placebo treatment.

The escape response to terminate vaginal distention, as described above, was assessed after 8 weeks.
Results The results indicate that vaginal hyperalgesia (increased sensitivity to pain) was induced in rats following uterus surgery. Escape response (i.e. time to response and number of responses within 15 seconds at a certain distention volume, compared to the control group) and vaginal pressure to different volumes of distention of the vaginal canal were determined. Results are shown from the four different experimental groups (the sham group values are used as baseline values) The relative reduction in escape response at 0.5 ml distension volume in relation to the sham treated group was
1. for the pulsed NAC treatment group: 32% reduction in escape response.
2. for the intermittent NAC treatment group: 28% reduction in escape response.
3. for the daily NAC treatment group: 18% reduction in escape response.

The results thus interestingly show that the pain reducing effect induced by NAC treatment was more marked in the pulsed treatment group and in the intermittent treatment group as compared to the group that received daily treatment.

It will be appreciated that the techniques and concepts discussed herein are not limited to the specific disclosed embodiments. The appended claims encompass all such changes and modifications as fall within the true spirit and scope of this invention.

We claim:

1. A method for the treatment of a mammal having endometriosis using a pharmaceutical composition comprising N-acetyl-L-cysteine; the method comprising:
   in a pulsed or intermittent dosage regimen,
   orally administering the pharmaceutical composition comprising N-acetyl-L-cysteine to the mammal for a time period of two months or more, at a dose of N-acetyl-L-cysteine that is between 20 and 90 mg/kg/day on administration days.

2. A method according to claim 1, wherein the pharmaceutical composition is administered for 3-5 consecutive days followed by 2-4 days of interruption.

3. A method according to claim 1, wherein the pharmaceutical composition is administered for 1-3 consecutive days, followed by 1-2 days of interruption.

4. A method according to claim 1, where the dose of N-acetyl-L-cysteine is between 30 and 60 mg/kg/day on administration days.

5. A method according to claim 1, where the dose of N-acetyl-L-cysteine is between 30 and 45 mg/kg/day on administration days.

6. A method according to claim 1, for treating pain caused by endometriosis.

7. A method according to claim 1, for treating infertility caused by endometriosis.

8. A method according to claim 1, for pre-treating mammals having endometriosis before laparoscopy or surgery.

9. A method according to claim 1, for treatment after laparoscopy or surgery, to prevent recurrences of endometriotic lesions.

* * * * *